(12) United States Patent
Carly

(10) Patent No.: US 7,081,116 B1
(45) Date of Patent: Jul. 25, 2006

(54) IMPLANT FOR OSTEOSYNTHESIS DEVICE IN PARTICULAR OF THE BACKBONE

(75) Inventor: Olivier Carly, Geneva (CH)

(73) Assignee: SCIENT'X, Guyancourt (FR)

( * ) Notice: Subject to any disclaimer, the term of this patent is extended or adjusted under 35 U.S.C. 154(b) by 537 days.

(21) Appl. No.: 10/009,998

(22) PCT Filed: Jun. 14, 2000

(86) PCT No.: PCT/FR00/01644

§ 371 (c)(1),
(2), (4) Date: Aug. 22, 2002

(87) PCT Pub. No.: WO00/76413

PCT Pub. Date: Dec. 21, 2000

(30) Foreign Application Priority Data

Jun. 14, 1999 (FR) .................................. 99 07687

(51) Int. Cl.
*A61B 17/70* (2006.01)
(52) U.S. Cl. .......................................... 606/61; 606/73
(58) Field of Classification Search .................. 606/60, 606/61, 72, 73
See application file for complete search history.

(56) References Cited

U.S. PATENT DOCUMENTS 5,716,356 A * 2/1998 Biedermann et al. ......... 606/61
5,885,286 A * 3/1999 Sherman et al. .............. 606/61

FOREIGN PATENT DOCUMENTS

| DE | 4425357 | 2/1996 |
| EP | 0836835 | 4/1998 |
| WO | WO9834554 | 8/1998 |
| WO | WO9841159 | 9/1998 |

* cited by examiner

*Primary Examiner*—Eduardo C. Robert
*Assistant Examiner*—Jessica R. Baxter
(74) *Attorney, Agent, or Firm*—Ladas & Parry LLP

(57) ABSTRACT

The invention relates to an implant for an osteosynthesis device, in particular for the spine, the implant including a first assembly itself including: a fixing body having a housing for receiving the head of an anchor screw in such a manner as to define a ball joint; and a positioning ring; and a second assembly itself including a nut type system. According to the invention: the first assembly has a positioning ring mounted in the fixing body; and the second assembly has a nut type system, adapted, when tightened on the body, to bear against the bracing rod and to cause the positioning ring to move in linear displacement.

11 Claims, 2 Drawing Sheets

IMPLANT FOR OSTEOSYNTHESIS DEVICE IN PARTICULAR OF THE BACKBONE

TECHNICAL FIELD

The present invention relates to the technical field of osteosynthesis, in particular of the spine, and more precisely it relates to an implant comprising anchor screws in the vertebrae, designed to make it possible to position angularly a bracing rod extending along said vertebrae for the purpose of holding them stationary during a period of bone fusion.

PRIOR ART

Various systems have been developed for correcting and stabilizing the spine and for facilitating bone fusion at various levels of the spine. In one such system, a rod is placed along the spine and is held in position by screws implanted in the vertebrae. The rod is suitable for being curved so as to follow the curvature of the region of the spine to which it is fitted. Thus, in order to comply with the anatomical shape of the spine, the bracing rod needs to be shaped so as to present considerable amounts of curvature, particularly in order to enable it to be installed relative to the lumbar and sacral vertebrae.

In order to make it possible for the rod to be shaped in this way while also ensuring that it is secured effectively to its anchor screws, proposals have been made to fit anchor screws with respective ball joints for receiving the bracing rod, so as to accommodate shape-following relative angles between the bracing rod and the anchor screws.

Thus, by way of example, European patent No. EP 0 614 649 describes an implant for an osteosynthesis device comprising a fixing body shaped in the form of a socket in which a reception channel is formed to receive a bracing rod. The fixing body is arranged to present a reception housing for the head of an anchor screw in order to define a ball joint between the anchor screw and the fixing body. That implant also has a positioning ring for placing between the head of the anchor screw and the bracing rod. The implant also has a nut type system for assembling the bracing rod to the fixing body. Such a system has a nut screwed onto the outside walls of the fixing body and a threaded lock screw is screwed into the inside of the fixing body. By screwing such an assembly device tight it is possible to clamp firstly the bracing rod between the lock screw and the positioning ring, and secondly the anchor screw between the positioning ring and the fixing body.

It must be considered that such an implant is made up of a plurality of parts that need to be built up into intermediate assemblies while the operation is taking place. This gives rise to difficulties of assembly and to installation time that is relatively lengthy.

Document DE 44 25 357 also describes an implant for an osteosynthesis device comprising a first assembly, itself comprising a fixing body arranged to present a reception housing for receiving the bead of an anchor screw in order to define a ball joint between the anchor screw and the fixing body. This first assembly also has a positioning ring for interposing between the head of the anchor screw and the bracing rod. That implant further comprises a second assembly, itself comprising a system of the nut type for assembling the bracing rod to the fixing body. Such an implant does not enable effective connection to be ensured between the anchor screw and the fixing body and therefore leads to the bracing rod being unstable relative to the anchor screw.

SUMMARY OF TE INVENTION

The object of the invention is thus to remedy the drawbacks of prior art implants by proposing an implant for an osteosynthesis device of the spine comprising a bone anchor screw fitted with a ball joint for receiving a bracing rod, such an implant being designed to be put into place quickly and easily, while also being adapted to enable an effective and durable connection to be made between the bracing rod and the bone anchor screw.

To achieve such an object, the implant for an osteosynthesis device, in particular of the spine, comprises:

a first assembly comprising:
a fixing body for a bracing rod, said body being arranged to present a reception housing for receiving an anchor screw head, thereby defining a ball joint between the anchor screw and the fixing body;
a positioning ring for interposing between the anchor screw head and the bracing rod;
and a second assembly comprising a nut type system for fastening the bracing rod to the fixing body.

According to the invention:
the first assembly has a positioning ring mounted in the fixing body with freedom to move in limited linear displacement and allowing the body and the anchor screw to rotate freely relative to each other in the absence of the bracing rod; and
the second assembly has a nut type system adapted on being screwed onto the body to bear against the bracing rod and move the positioning ring in linear manner so that on being tightened it clamps the bracing rod between said system and the positioning ring, and also clamps the anchor screw between the positioning ring and the fixing body.

Various other characteristics appear from the following description given with reference to the accompanying drawings which show embodiments and implementations of the invention as non-limiting examples.

BEST MANNER OF PERFORMING THE INVENTION

Figure 1:
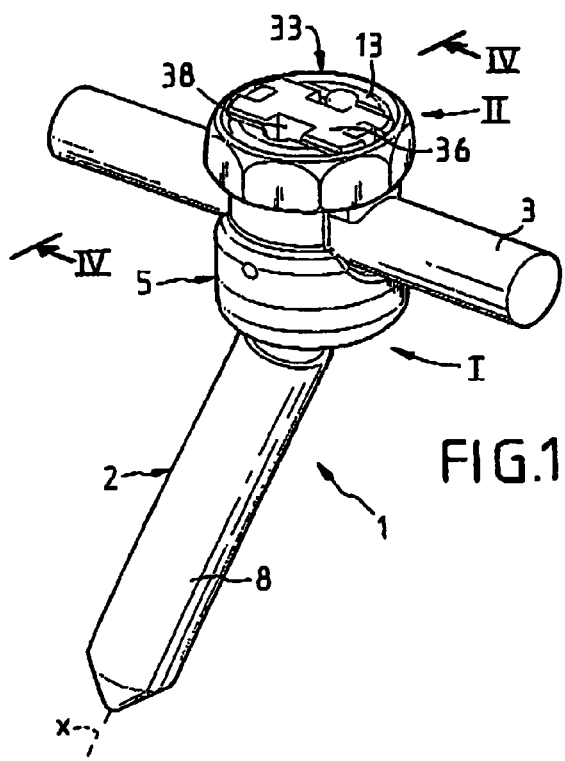
FIG. 1 is a perspective view showing a complete implant receiving an intervertebral bracing rod.

The implant 1 shown in FIG. 1 is for an osteosynthesis device (not shown) in particular for the spine. In accordance with the invention the implant 1 is constituted by a first assembly I comprising, in particular, a bone anchor screw 2, and by a second assembly II designed to secure an intervertebral bracing rod 3 relative to the anchor screw 2.

Figure 2:
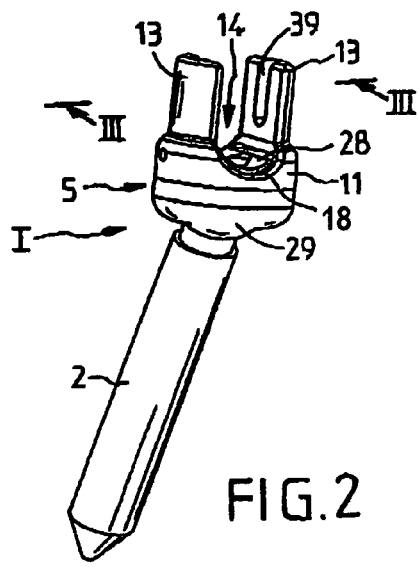
FIG. 2 is a perspective view of a first assembly forming the implant of the invention.
Figure 3:
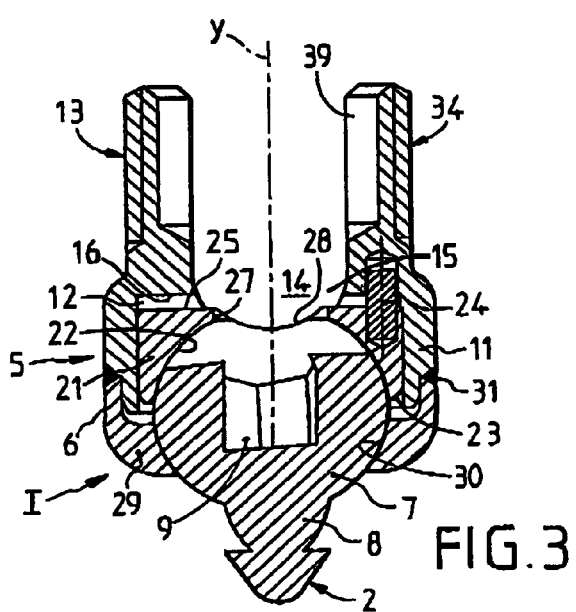
FIG. 3 is a section view in elevation of the first assembly, taken substantially on lines III—III of FIG. 2.

As can be seen more clearly in FIGS. 2 and 3, the first assembly I comprises a fixing body 5 arranged to present a reception housing 6 for receiving the head 7 of the anchor screw 2 which extends beyond the end of a threaded anchor rod 8 of longitudinal axis x. In conventional manner, the head 7 of the anchor screw 2 is generally in the form of a sphere truncated at its summit and provided with a blind hole 9 of polygonal section to enable the anchor screw 2 to be turned by means of a screw-driving tool that is not shown but that is conventional.

In the example shown, the fixing body 5 has a head 11 constituted in the form of a socket on a longitudinal axis y, with a cavity 12 formed therein centered on the longitudinal axis y. In a preferred embodiment, two diametrally-opposite side branches or walls 13 project from the fixing head 11 so as to define between them a reception channel 14 for receiving the bracing rod 3. The cavity 12 opens out into the channel 14 between the side branches 13, via an orifice 15 formed through the bottom 16 of the cavity 12. The reception channel 14 opens out on either side of the head 5 in a direction that is perpendicular to the diametral plane of symmetry containing the side branches 12. The reception channel 14 is preferably arranged in the top portion of the fixing head 11 so as to have a notch 18 of semicircular profile to enable part of the bracing rod 3 to be received therein, such a rod conventially being of circular cross-section.

The first assembly I also has a positioning ring 21 for interposing between the head 7 of the anchor screw and the bracing rod 3. This positioning ring 21 is mounted inside the cavity 12 and has a central bore 22 of partly spherical shape opening out via a first transverse face 23 for cooperating with the top portion of the head 7 of the anchor screw. Naturally, the greatest diameter of the central bore 22 is smaller than the diameter of the head 7 of the anchor screw. The positioning ring 21 is capable of limited displacement along the axis of symmetry y of the body 5 between the bottom 16 of the cavity 12 and the head 7 of the anchor screw. In a preferred embodiment, the positioning ring 21 is guided to move with limited linear displacement along the longitudinal axis y. In the example shown, the ring 21 is guided to move in linear displacement by means of a guide peg 24 interposed between the fixing body 5 and the positioning ring 21. For example, the guide peg 24 is engaged in blind bores formed in the bottom 16 of the cavity 12 and a second transverse face 25 of the positioning ring extending facing the bottom 16 of the cavity.

It should be observed that the central bore 22 of the positioning ring 21 opens out via a through opening 27 into the second transverse face 25 so as to communicate with the orifice 15 formed in the head 11, thereby providing access for a screw-driving tool to the blind hole 9 in the anchor screw. The second transverse face 25 of the positioning ring 21 preferably presents a concave surface 28 complementary to the bracing rod 3. This concave surface 28 thus forms a kind of cradle continuing the notch 18 so as to define a portion of the reception channel 14 for receiving the bracing rod 3. It should be observed that the concave face 28 lies automatically in line with the notches 18 for receiving the bracing rod 3 given that the positioning ring 21 is guided in linear displacement along the longitudinal axis y.

As can be seen more clearly in FIG. 3, the anchor screw 2 is held assembled to the fixing body 5 by means of a closure cup 29 fixed to the fixing head 11. This closure cup 29 possesses a central bore 30 of part spherical shape complementary to the profile of the bottom portion of the head 7 of the anchor screw. The central bore 30 possesses a maximum diameter which is naturally smaller than the diameter of the head 7 of the anchor screw. In the example shown, the closure cup 29 is fixed to the fixing head 11 by means of a peripheral bead of welding 31. The anchor screw 2 is thus mounted to the fixing body 5 via a ball joint malting it possible for the fixing body 5 and the anchor screw 2 to move angularly relative to each other within a cone. The head 7 of the anchor screw 2 thus co-operates with the internal bores 22, 30 respectively of the positioning ring 21 and of the closure cup 29 so that together they define the housing 6 for guiding the head 7 of the anchor screw in rotation.

The way the assembly I is put together stems directly from the description above. The fixing head 11 is designed to receive the positioning ring 21 in the cavity 12, while ensuring that the guide peg 24 is engaged between the positioning ring 21 and the fixing head 11. The internal bore 30 of the closure cup 29 is engaged on the threaded end 8 of the anchor screw 2 and moves up to the head 7. The head 7 of the anchor screw 2 is inserted into the internal bore 22 of the positioning ring 21. The closure cup 29 has the anchor screw 2 passing through it and it is fixed to the fixing head 11 by welding in the example shown. It should be observed that in the absence of the bracing rod 3, the positioning ring 21 is free to move in linear displacement over a limited stroke so as to allow the head 7 of the anchor screw 2 to rotate relative to the fixing body 5.

It should be understood that the anchor screw 2 is assembled to the fixing body 5 prior to being used. Thus, the assembly I is presented in the form of a single unit ready for directly receiving the bracing rod 3 which is fixed to the fixing body 5 by means of the second assembly II which is a nut type fastener. In a preferred embodiment, the fastener assembly II is a nut 33 of the type described in patent application WO 98/41159.

Figure 4:
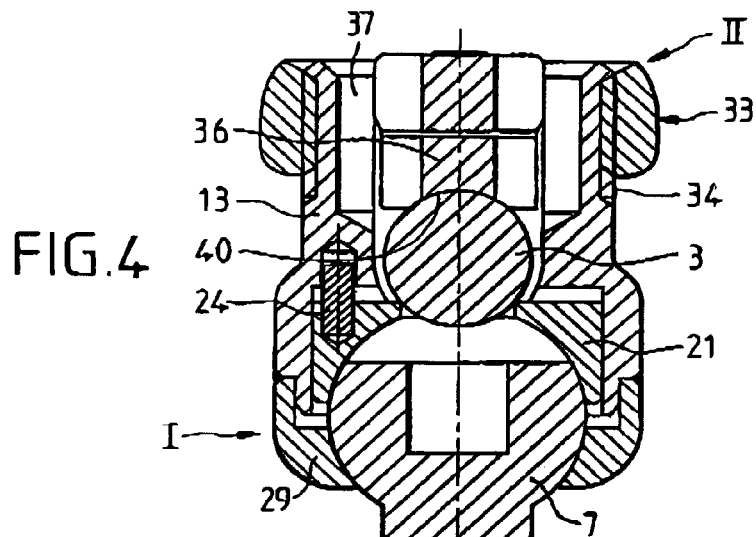
FIG. 4 is a section view in elevation of an implant of the invention taken substantially on lines IV—IV of FIG. 1.
Figure 5:
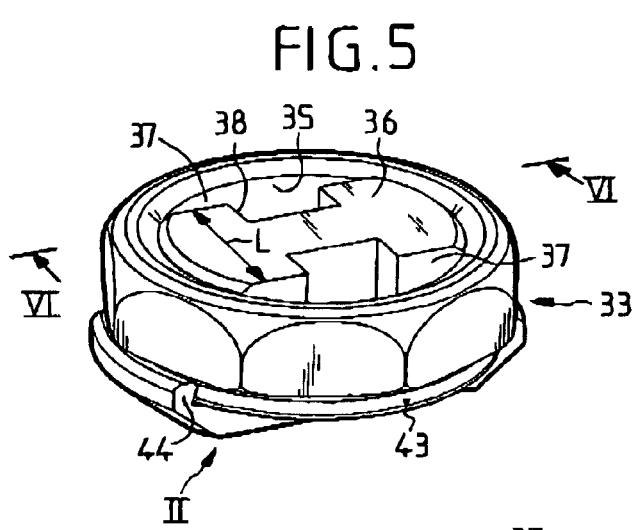
FIG. 5 is a perspective view of a second assembly making up the implant of the invention.
Figure 6:
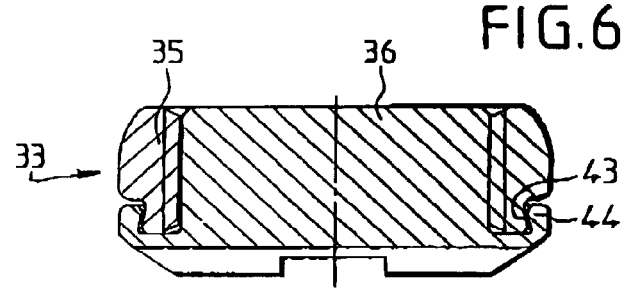
FIG. 6 is a section view of a second assembly, taken substantially on lines VI—VI of FIG. 5.

In this preferred embodiment shown more particularly in FIGS. 4 to 6, the side branches 13 have outside walls 34 inscribed within a circle and threaded to receive the nut 33 which, in conventional manner, has a polygonal outside section to enable it to be held by an appropriate tool. The nut 33 has tapping 35 for screwing onto the threaded walls 34 of the side branches 13.

The nut 33 is fitted with a shoe 36 extending diametrally across the tapping 35 and mounted free to rotate relative to the nut 33 so as to come to bear against the bracing rod 3 in order to hold it in place by being tightened between said shoe 36 and the positioning ring 21. The width L of the shoe 36 is adapted to leave two gaps 37 on either side, each serving to pass one of the side branches 13 of the fixing body 5. The gaps 37 also make it possible to insert the two pins of a tool (not shown) for taking hold of the nut 33. The pins of the tool can be positioned by engaging them in notches 38 formed in the sides of the shoe 36. In order to enable the pins of the tool to be guided and consequently to enable the shoe 36 to be indexed between the side branches 13 even while it is out of sight, the inside walls of the side branches 13 have respective longitudinal slots 39 extending from the free ends of the branches 13 as far as the fixing head 11. Advantageously, the shoe 36 has an inside transverse surface 40 that is concave and complementary to the top surface of the bracing rod 3.

In an advantageous characteristic shown in FIGS. 5 and 6, the shoe 36 is snap-fastened to the nut 33. As can be seen in FIGS. 5 and 6, the nut 33 has a peripheral groove 43 formed at the base of the nut for receiving ribs 44 extending from opposite ends of the shoe 36 and suitable for deforming elastically so as to snap-fasten in the groove 43.

The way the implant 1 of the invention, made up of two assemblies 1 and 11, is used sterns directly from the above description.

The assembly I without the assembly II is initially used for implanting the anchor screw 2 in a determined vertebra. Thereafter, the bracing rod 3 is placed so as to be inserted between the side branches 13 of the fixing body 5. Given the freedom for relative rotation between the anchor screw 2 and the fixing body 5, the bracing rod 3 positions itself automatically inside the reception channel 14 of the body 5.

Thereafter, the nut 33 is screwed onto the outside walls 34 of the side branches 13 with the shoe 36 being engaged between the branches 13. Tightening the nut 33 causes the shoe 36 to move so as to come to bear against the bracing rod 3. Continued tightening leads to the positioning ring 21 being subjected to limited linear displacement so as to exert a force on the head 7 of the anchor screw 2. Such tightening of the nut 33 leads to the anchor screw 2 being clamped between the positioning ring 21 and the closure cup 29, and also to the bracing rod 3 being clamped between the shoe 36 and the positioning ring 21. It should be observed that tightening the nut 33 onto the outside walls 34 of the side branches 13 ensures that they cannot splay apart when the shoe 36 applies a thrust force on the bracing rod 3. This assembly makes it possible to obtain large contact area between the shoe 36 and the bracing rod 3, thereby giving rise to effective and long-lasting clamping of the bracing rod 3 relative to the fixing body 5.

The invention is not limited to the examples described and shown since various modifications can be applied thereto without going beyond the ambit of the invention.

What is claimed is:

1. An implant for an osteosynthesis device, in particular for the spine, the implant comprising:
    a first assembly comprising:
        a fixing body for a bracing rod, said body being arranged to present a reception housing for receiving an anchor screw head, thereby defining a ball joint between the anchor screw and the fixing body;
        a positioning ring for interposing between the anchor screw head and the bracing rod;
    and a second assembly comprising a nut type system for fastening the bracing rod to the fixing body,
    wherein
    the first assembly has a positioning ring mounted in the fixing body with freedom to move in limited linear displacement and allowing the body and the anchor screw to rotate freely relative to each other in the absence of the bracing rod; and
    the second assembly has a nut type system adapted on being screwed onto the body to bear against the bracing rod and move the positioning ring in linear manner so that on being tightened it clamps the bracing rod between said system and the positioning ring, and also clamps the anchor screw between the positioning ring and the fixing body;
    wherein the positioning ring is guided to move with limited linear displacement relative to the fixing body by means of a guide peg co-operating with a complementary bore.

2. An implant according to claim 1, wherein:
    the fixing body has two side branches defining a channel between them that opens out on either side of the body in order to receive the bracing rod, the side branches having outside walls that are threaded; and
    the fastening system comprises a nut adapted to be screwed onto the outside threaded walls of the side branches, the nut being fitted in its diametral zone with a shoe mounted to rotate freely and designed to come to bear against the bracing rod so that when tightened it clamps said shoe and the positioning ring.

3. An implant according to claim 1, wherein the positioning ring presents a concave surface complementary to the bracing rod and is guided to slide in such a manner that the concave surface defines a portion of the reception channel for receiving the bracing rod so as to ensure that the bracing rod is positioned automatically between the side branches and on the positioning ring.

4. An implant according to claim 2 or 3, wherein the positioning ring presents a through opening opening out between the side walls and over the head of the anchor screw in which there is provided a blind hole suitable for receiving a screw-driver tool passing through the opening.

5. An implant according to claim 1 or 2, wherein the fixing body comprises:
    a fixing head on which there stands the two side branches and in which there is arranged a cavity opening out at one end between the side branches and opening out at its opposite end;
    the positioning ring mounted to move with limited displacement inside the cavity with its surface for receiving the bracing rod opening between the two side branches;
    the head of the anchor screw mounted at least in part inside the cavity so that the positioning ring is interposed between said head and the body; and
    a closure cup fixed on the fixing body on its inside face to close the cavity and having the anchor screw passing therethrough.

6. An implant according to claim 1, wherein the positioning ring and the closure cup present partly-spherical bores so as to define the reception housing for receiving the head of the anchor screw.

7. An implant according to claim 1, wherein the nut has a shoe of width adapted to co-operate with the nut to define on either side of the shoe two gaps serving firstly to receive the two pins of a tool for taking hold of the nut, and secondly to pass the side branches of the fixing body in order to enable said shoe to slide between the side branches.

8. An implant according to claim 2 or 7, wherein the fixing body has two slots arranged facing each other in the inside walls of the side branches so that once the bracing rod has been installed they guide the pins of the tool on the fixing body and they enable the shoe to be indexed while out of sight between the side branches.

9. An implant according to claim 8, wherein the nut has a shoe with two notches being formed on the side edges thereof, said notches opening out into the gaps and being designed to receive and position pins of the tool.

10. An implant according to claim 7, wherein the nut has means enabling the shoe to be mounted by snap-fastening, which shoe is free to rotate relative to the nut once it has been mounted.

11. An implant according to claim 4, wherein the positioning ring and the closure cup present partly-spherical bores so as to define the reception housing for receiving the head of another screw.

* * * * *